SPUR-TYPE SOUR CHERRY TREE

Filed April 19, 1971 3 Sheets-Sheet 1

INVENTOR,
FRANCIS WARREN CARNEFIX
BY

Christensen & Sanborn
ATTORNEYS

SPUR-TYPE SOUR CHERRY TREE

Filed April 19, 1971 3 Sheets-Sheet 2

INVENTOR,
FRANCIS WARREN CARNEFIX
BY
Christenson & Sanborn
ATTORNEYS

SPUR-TYPE SOUR CHERRY TREE

Filed April 19, 1971 3 Sheets-Sheet 3

INVENTOR,
FRANCIS WARREN CARNEFIX
BY

Christensen & Sanborn
ATTORNEYS

United States Patent Office

Plant Pat. 3,304
Patented Feb. 13, 1973

3,304

SPUR-TYPE SOUR CHERRY TREE

Francis Warren Carnefix, Fruitland, Idaho 83619

Filed Apr. 19, 1971, Ser. No. 135,323
Int. Cl. A01h 5/03
U.S. Cl. Plt.—37 1 Claim

ABSTRACT OF THE DISCLOSURE

A spur-type sour cherry tree is disclosed constituting a mutation of the standard Montmorency.

DESCRIPTION

This invention or discovery relates to a new and distinct variety of sour cherry tree. The nearest related variety is the standard Montmorency sour red cherry tree. The new variety initially appeared and was discovered growing as a scaffold sport limb on a mature Montmorency tree growing in an orchard located approximately 300 feet south of the section line along the boundary of Highway 95 in Section 2, Township 9 North, Range 5, west of the Boise Meridian, Payette County, Idaho. Reproduciton of the new tree at the applicant's orchard approximately ten miles from the parent tree, at substantially the same elevation and under substatnially the same climatic and soil conditions, enabled comparison of reproduction stock with standard Montmorency trees adjacent thereto and with the original sport limb remaining on the parent tree. Observations under these conditions have established the genetic stability and afforded a basis of comparison of the new variety with the parent..

In the drawings FIG. 1 is a photograph showing at the left an uprooted standard Montmorency with approximately the top one-fourth blanked out for convenience in illustration, and at the right an uprooted tree of the new variety, same age, with approximately the top one-twentieth blanked out for illustrative convenience. In both cases the trees grew on standard Mahaleb cherry root stock.

*Bark and wood*

The bark and wood of the new variety appear to be the same in color, texture, fiber structure, and other characteristics as those of the standard Montmorency.

*Tree and branch structure*

The tree is of sturdy, spreading, upright growth and normally tends to be of wider spread and about three-fourths the height of the standard Montmorency tree of the same age. The limb-to-trunk and limb-to-limb crotch angles are wider in the new tree and the branches thicker and stiffer than in the standard tree, affording materially greater protection against wind damage due to whip and inter-branch contact. The main branches, though turning upward at the ends, leave the trunk at more nearly horizontal directions with the new variety than with Montmorency.

The branches are well spaced and spurring is heavy. Spurring averaged about 13 per foot of branch length with the new variety as compared with about 5 per foot with the Montmorency. The branches are somewhat shorter and more compact than those of Montmorency.

The leaf and fruit spurs forming along the branches of the new variety remain throughout ripening and dormancy, whereas with Montmorency the spurs which form initially along the branches tend to shed off along stretches between nodes so that approaching ripening only localized clumps of fruit and leaves occur at nodules of the standard tree branches, whereas for a given length of branch a much higher fruit yield and leaf cover remains on the new variety.

*Roots*

Figure 1:
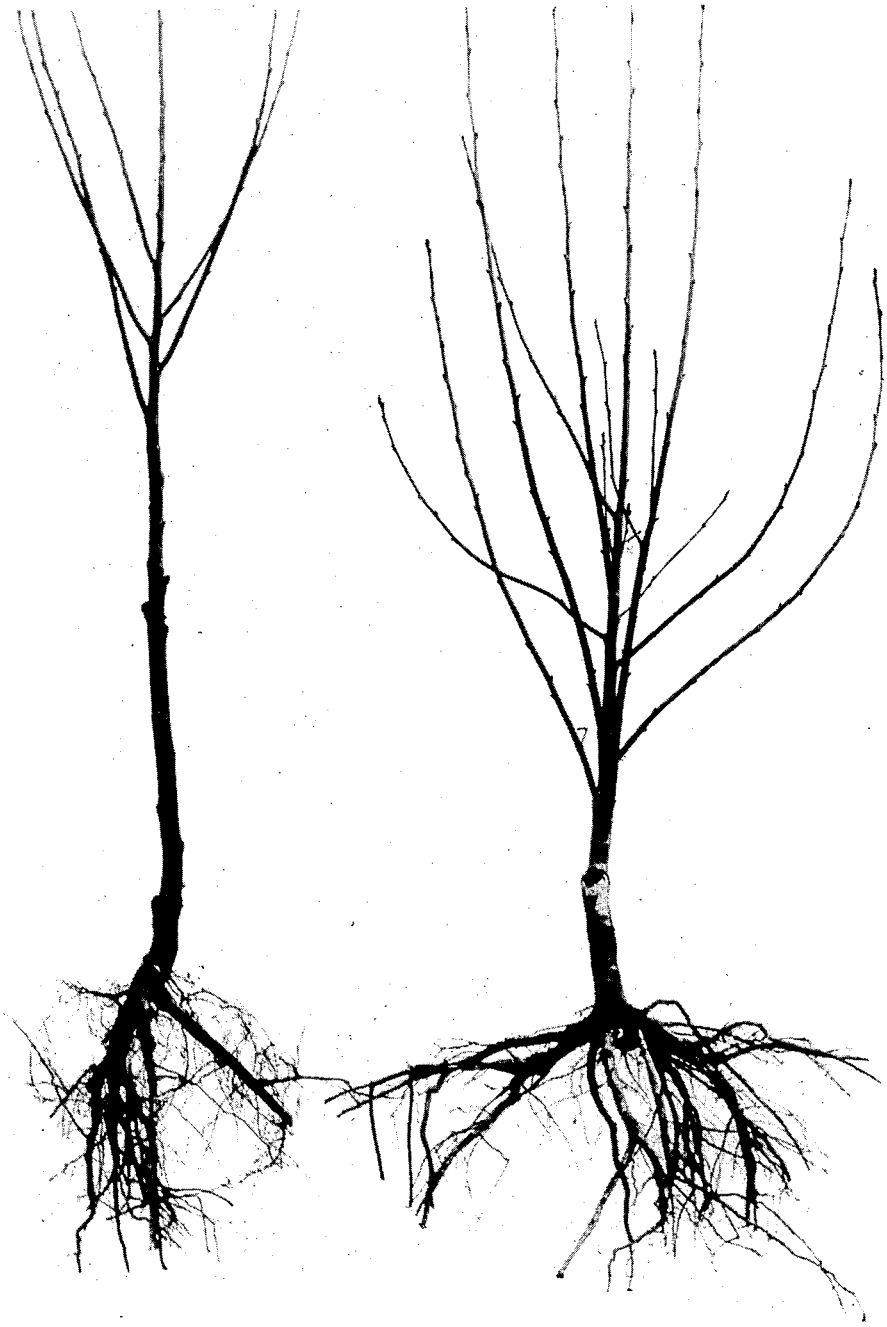
Figure 2:
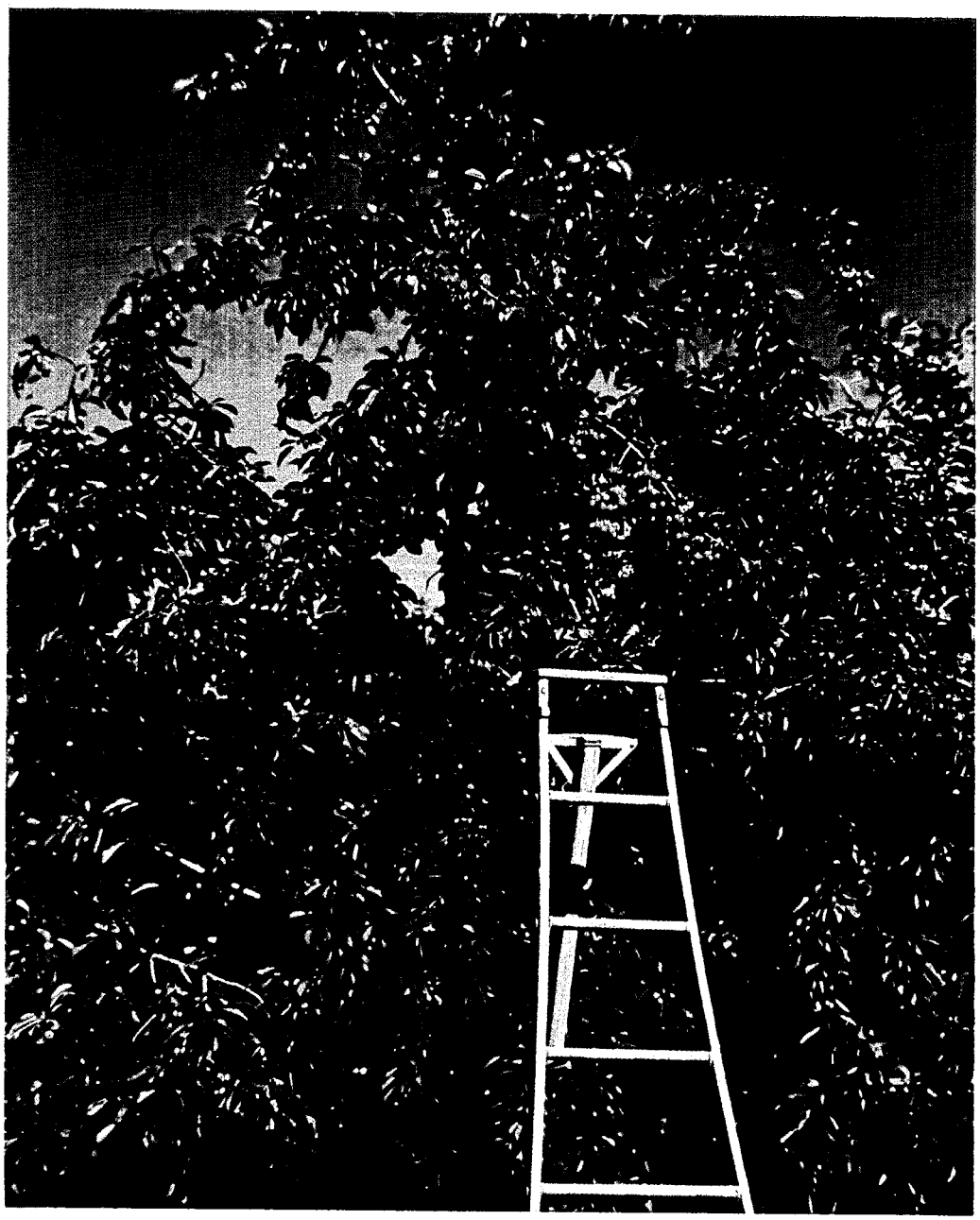
FIG. 2 is a photograph showing the parent Montmorency tree with the sport scaffold limb of the new variety growing upwardly in the top central portion of the photograph, above the stepladder shown, the tree being photographed with the fruit mature and ready for picking.
Figure 3:
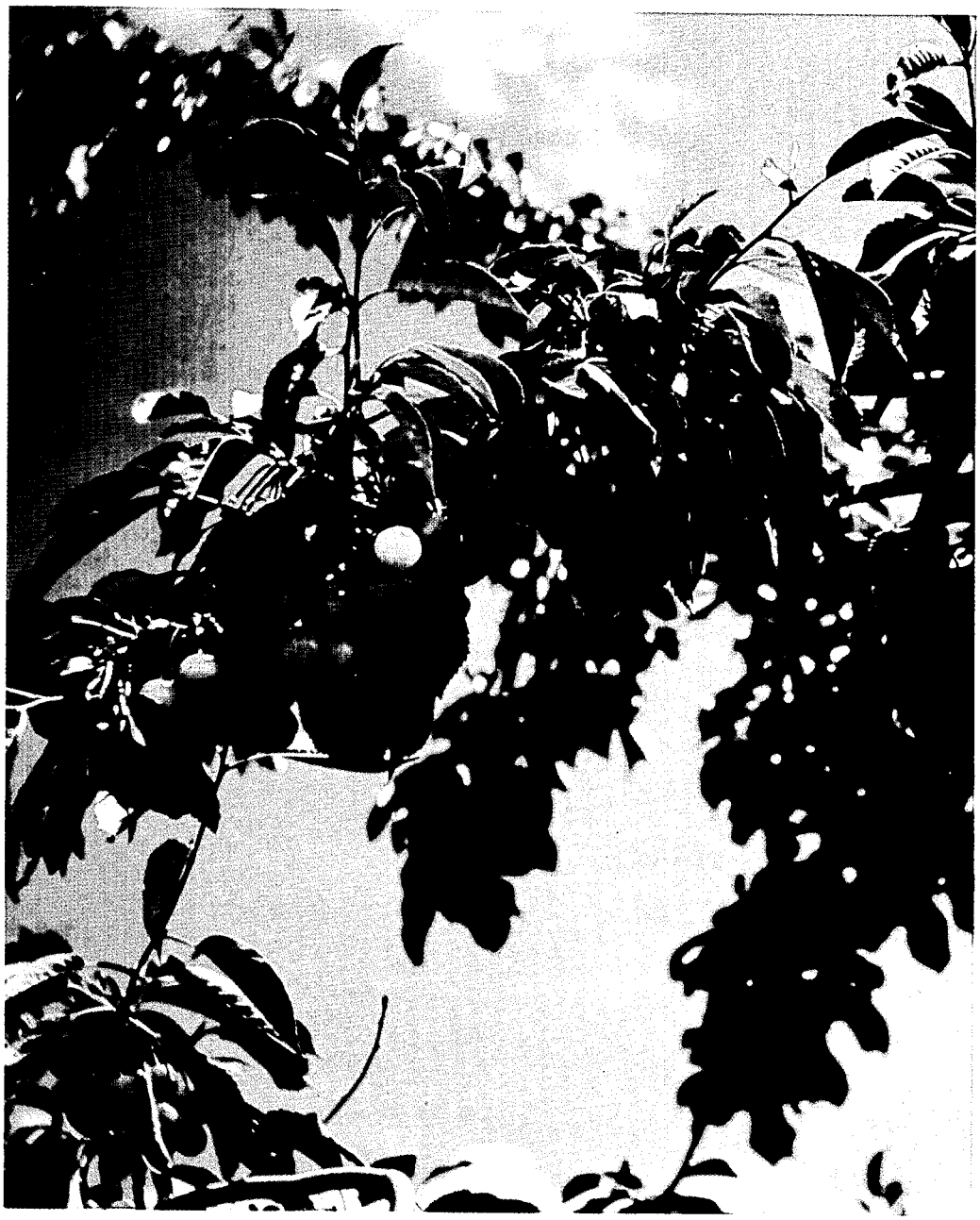
FIG. 3 is a close-up view of a portion of the scaffold limb system of the new variety shown in FIG. 2.

As will be seen in FIG. 1, the new variety produces a root structure which is heavier and more spreading than that of the standard variety.

*Fruit*

The fruit of the new variety ripens about the same time or a day later than that of Montmorency. It develops a somewhat heavier concentration of soluble solids (about 18% as compared with 16% for Montmorency), presumably because of the better exposure of the fruit to scatter light and air and better protection by the leaves against sunburn of the fruit. The fruit of the new variety is about the same size at maturity as that of standard Montmorency fruit. In flavor, texture and appearance (i.e., shape and color) the fruit is also similar to that of Montmorency. The total amount of fruit produced by trees of the same age appears to be about the same with the new variety as with the standard Montmorency.

*Leaves*

The leaves of the new variety are much more numerous and more closely spaced in characteristic spur clusters than with Montmorency. In these clusters they are stacked five or six deep on the average in the new variety and only one or two deep in the standard Montmorency. They are much greener; that is, they have a substantially heavier chlorophyll concentration than the leaves of Montmorency. They are more rounded in outline shape and at the ends taper abruptly to sharper points than Montmorency leaves. On the average they measure in length along the mid rib from about 5.5 to 7.0 cm., whereas standard Montmorency leaves measure from about 6.5 to 9.0 cm. in length. The new variety leafs out somewhat earlier and the leaves develop faster than those of the standard Montmorency.

*Blossoms*

The new variety typically blossoms about four days later than the parent variety, thereby making it less vulnerable to frost damage. The blossoms of the two varieties are similar in appearance.

I claim as my invention or discovery:

1. The new and distinct variety of sour cherry tree which as herein illustrated and described in relation to the standard Montmorency, the nearest related variety, is characterized in part by its dense fruit and leaf spurring characteristics; its sturdy, spreading upright growth; its wide crotch angles; its deep green and numerous leaves of rounded shape sharply pointed at the ends; its slightly smaller fruit richer in soluble solids; its heavy and spreading root structure; and its somewhat later blossoming period.

No references cited.

ROBERT E. BAGWILL, Primary Examiner